(12) United States Patent
Franz

(10) Patent No.: US 9,585,967 B2
(45) Date of Patent: Mar. 7, 2017

(54) NICOTINE-CONTAINING PRODUCT

(75) Inventor: Alexander Franz, Reiden (CH)

(73) Assignee: SIEGFRIED LTD., Zofingen (CH)

( * ) Notice: Subject to any disclaimer, the term of this patent is extended or adjusted under 35 U.S.C. 154(b) by 388 days.

(21) Appl. No.: 13/058,778

(22) PCT Filed: Dec. 10, 2009

(86) PCT No.: PCT/EP2009/008822
§ 371 (c)(1),
(2), (4) Date: Mar. 15, 2011

(87) PCT Pub. No.: WO2010/069507
PCT Pub. Date: Jun. 24, 2010

(65) Prior Publication Data
US 2011/0207782 A1   Aug. 25, 2011

(30) Foreign Application Priority Data
Dec. 19, 2008  (EP) .................... 08022123

(51) Int. Cl.
| A61K 31/44 | (2006.01) |
| A61K 31/715 | (2006.01) |
| A61K 47/00 | (2006.01) |
| A61K 47/48 | (2006.01) |
| A61K 9/68 | (2006.01) |
| A61K 9/70 | (2006.01) |

(52) U.S. Cl.
CPC ...... *A61K 47/48184* (2013.01); *A61K 9/0058* (2013.01); *A61K 9/7023* (2013.01)

(58) Field of Classification Search
USPC ......... 514/277, 359, 23, 58, 772.1, 777, 343
See application file for complete search history.

(56) References Cited

U.S. PATENT DOCUMENTS

| 3,807,414 A * | 4/1974 | Hedge ............................ 131/359 |
| 3,845,217 A | 10/1974 | Ferno et al. |
| 3,901,248 A | 8/1975 | Lichtneckert et al. |
| 4,368,322 A * | 1/1983 | Muzzarelli ...................... 536/20 |
| 5,935,604 A | 8/1999 | Illum |
| 2003/0224048 A1 | 12/2003 | Walling |
| 2005/0123502 A1 | 6/2005 | Chan et al. |
| 2011/0165253 A1 * | 7/2011 | Roehrich ....................... 424/489 |

FOREIGN PATENT DOCUMENTS

| GB | 2 385 288 A | 8/2003 |
| WO | WO 03/101982 A1 | 12/2003 |
| WO | WO 2005/053691 A2 | 6/2005 |
| WO | WO 2007/133140 A1 | 11/2007 |
| WO | WO 2007/133141 A1 | 11/2007 |

\* cited by examiner

*Primary Examiner* — Shobha Kantamneni
(74) *Attorney, Agent, or Firm* — Oliff PLC

(57) ABSTRACT

A nicotine-containing product comprising a pharmaceutically acceptable polymeric substrate, which is able to bind cations, nicotine or a pharmaceutically acceptable nicotine derivative, and pharmaceutically acceptable inorganic cations. It further pertains to a method for the preparation of such a nicotine-containing product and to the use thereof for the preparation of a pharmaceutical product.

9 Claims, No Drawings

NICOTINE-CONTAINING PRODUCT

The present invention relates to a nicotine-containing product, a method for the production thereof, and its use for the preparation of a nicotine-containing pharmaceutical product.

Nicotine, or (S)-3-(1-Methyl-2-pyrrolidinyl)pyridine, is an alkaloid found in the nightshade family of plants (Solanaceae), predominantly in tobacco and coca, and in lower quantities in tomato, potato, eggplant, and green pepper. Nicotine has been found to constitute approximately 0.6-3.0% of dry weight of tobacco, with biosynthesis taking place in the roots, and accumulating in the leaves. It functions as an antiherbivore chemical, being a potent neurotoxin with particular specificity to insects; therefore, nicotine was widely used as an insecticide in the past.

Nicotine is a hygroscopic, oily, colorless or pale yellow liquid, which is miscible with water in its base form. It is characterized by a pyridine odor, a molecular weight of about 162 g/mol, an octanol:water partition coefficient (log P) of about 1.2, dissociation constants $pK_1$ of 6.16 and $pK_2$ of 10.96, and a melting point of approximately −79° C. As a nitrogenous base, nicotine forms salts with acids, which are usually solid and water soluble.

Nicotine and nicotine derivatives are readily absorbed from the gastro-intestinal tract, the buccal mucosa, the respiratory tract, and intact skin, and widely distributed throughout the tissues. Nicotine undergoes extensive first-pass metabolism when administered orally, thus reducing the bioavailability. Oral bioavailability of nicotine is about 30%. Furthermore, nicotine easily penetrates the skin. As nicotine enters the body, it is distributed quickly through the bloodstream and can cross the blood-brain barrier. The half life of nicotine in the body is around two hours. It is metabolized in the liver by cytochrome P450 enzymes, a major metabolite being cotinine.

In low concentrations (an average cigarette yields about 1 mg of absorbed nicotine), the substance acts as a stimulant in mammals and is one of the main factors responsible for the dependence-forming properties of tobacco smoking. Nicotine binds stereo-selectively to nicotinic-cholinergic receptors on autonomic ganglia, the adrenal medulla, neuromuscular junctions, and in the brain. It exerts two effects, a stimulant effect exerted at the locus ceruleus and a reward effect in the limbic system: By binding to CNS type nicotinic receptors, nicotine increases dopamine levels in the reward circuits of the brain. In this way, it activates the sympathetic nervous system and generates feelings of pleasure. Binding of nicotine to ganglion type nicotinic receptors, on the other hand, increases flow of adrenaline, a stimulating hormone. The release of adrenaline causes an increase in heart rate, blood pressure, and respiration, as well as higher blood glucose levels. Nicotine is a highly addictive substance. In high doses, nicotine will cause blocking of the nicotinic acetylcholine receptor, which is the reason for its toxicity and its effectiveness as an insecticide.

The primary therapeutic use of nicotine and nicotine derivatives is in treating nicotine dependence in order to cease smoking. Controlled levels of nicotine or a nicotine derivative are given to patients through gums, dermal patches, creams, lozenges, electric/substitute cigarettes or nasal sprays in an effort to wean them off their dependence. Nicotine has also been found therapeutically valuable in the treatment of other conditions involving release of dopamine, such as attention deficit hyperactive disorder (ADHD), attention deficit disorder (ADD), Tourette's syndrome, schizophrenia, Alzheimer's disease, Parkinson's disease, ulcerative colitis, anxiety, and depression; in the therapeutic angiogenesis and vasculogenesis; in the treatment of inflammatory bowel disease and autosomal dominant nocturnal frontal lobe epilepsy. Nicotine inhalers and patches are mainly used to treat smoking withdrawal syndrome.

Nicotine in its base form is readily absorbed through oral mucosa but is highly volatile and subject to oxidative degradation. By the action of air or light, nicotine is oxidized and turns brown. Due to its high toxicity, its low stability and its strong odor, handling of pure nicotine is highly demanding. Furthermore, the protection of staff and environment is fairly demanding with regard to production, transport and storage equipment.

In order to Circumvent these problems, several alternatives to nicotine in its base form have been developed. Especially (pharmaceutically acceptable) nicotine salts and complexes offer great advantages: The available nicotine salts are more stable compounds and are not as readily absorbed as the free base. They are usually solid, stable and have a low vapor pressure.

Several compositions containing nicotine or nicotine derivatives are known as active ingredients for pharmaceutical compositions:

GB 2 385 288 discloses a method for loading a resin with an active substance, such as nicotine. This method comprises blending nicotine with a resin and a solvent to obtain a nicotine-resin complex.

U.S. Pat. No. 3,901,248 discloses a smoking substitute composition based on a gum. As the active ingredient, a nicotine-cation exchange resin complex is dispersed in the gum base. The nicotine-resin complex constitutes up to about 10% of the chewing gum composition and affords a nicotine release when chewed of approximately that available when smoking a conventional cigarette.

U.S. Pat. No. 5,935,604 pertains to a nasal drug delivery composition comprising nicotine or a pharmacologically acceptable salt or derivative thereof. The composition is adapted to delivery of a pulse of nicotine for rapid absorption and a controlled release of nicotine and subsequent sustained absorption. The controlled release phase is achieved by providing a cation exchange material which forms a complex with the nicotine.

For an ideal smoking substitute, the release of nicotine should take place rather uniformly during not to short a period of time. In addition, nicotine should be substantially uniformly distributed within the pharmaceutical composition. In order to avoid undesired side effects based on nicotine dependence when ceasing to smoke, it is important that the nicotine level in the blood stream reaches a certain minimal concentration as fast as possible. To this end, the United States Pharmacopeia (USP) requires a nicotine release rate of at least 70% within ten minutes. In order to achieve such a high release rate, it has so far been necessary to use nicotine-containing products with fairly high nicotine concentration. However, high nicotine contents may cause adverse side effects, such as a bitter taste or irritation of the treated area.

In order to overcome these problems, it is known to use nicotine resin complexes, which also comprise polyols:

WO 03/101982 discloses a nicotine-containing composition having a controlled release rate of nicotine and a method for the preparation thereof. The nicotine-containing composition is based on a cation exchange resin and has a release rate of nicotine of at least 70% over a ten minute period. In order to achieve such a high release rate, the product is prepared by treating the cation exchange resin with an organic polyol, followed by application of nicotine to form a nicotine coated cation exchange resin mixture.

US 2003/0224048 discloses a nicotine product having a nicotine release rate of not less than 70% over a ten minute period, as well as a process to produce such a product. Again, a cation exchange resin is treated with an organic polyol and nicotine.

WO 2005/053691 relates to a nicotine delivery product and a method for the production thereof. The nicotine delivery products comprise the reaction product of a nicotine cation exchange resin complex and an organic polyol. It is particularly suited for use in smoking substitution devices delivering nicotine, such as chewing gums, patches, lozenges, melting tablets, and tablets for chewing.

Thanks to the polyol additives, the above compositions achieve the desired controlled release rates for nicotine. However, possible side effects of these polyol additives have not been studied in detail yet, and it is not known, whether there are any toxicity issues or other adverse side effects. For this reason, it would be desirable to provide a nicotine-containing pharmaceutical product, which allows for a controlled release rate of nicotine, without necessitating polyol additives or high nicotine contents.

The problem is solved by the nicotine-containing product according to claim 1 and the method for producing such a nicotine-containing product according to claim 10. Furthermore, the present invention also pertains to the use of the nicotine-containing product for the preparation of a nicotine-containing pharmaceutical product. Preferred embodiments are described in the dependent claims.

The nicotine-containing product of the present invention comprises
(a) a pharmaceutically acceptable polymeric substrate, which is able to bind cations,
(b) nicotine or a pharmaceutically acceptable nicotine derivative, and
(c) pharmaceutically acceptable inorganic cations.

The nicotine-containing product of the present invention is based on a polymeric substrate. This substrate "is able to bind cations", i.e. organic and inorganic cations can be stored in the substrate. The cations can be bound to the polymeric substrate by covalent or ionic bonds or by van der Waals interactions, or they can be absorbed in cavities within the polymeric structure of the substrate.

The nicotine-containing product of the present invention allows for a controlled release of nicotine: Not only is the desired release rate of 70% within ten minutes achieved, but there are also no extreme peak releases, which would cause side effects such as a bitter taste or irritation of the treatment site. The pharmaceutically acceptable inorganic cations are well known and have no undesired side effects. It is therefore no longer necessary to use the potentially harmful polyol additives. In addition, the nicotine content required for the desired release rate has been lowered considerably, thus leading to lower material costs and risk-reduced production procedures.

In a preferred embodiment, the pharmaceutically acceptable polymeric substrate is selected from the group consisting of cation exchange resins and polysaccharides. Preferably, the pharmaceutically acceptable substrate is a weakly acidic cation exchange resin selected from the group consisting of Amberlite® IR-20, Amberlite® IRP-69, Amberlite® IPR-64, Amberlite® IRP-58, Amberlite® IRC-50, and Amberlite® IRP-69, most preferably Amberlite® IPR-64, which is also called Polacrilex. Alternatively, polysaccharides, such as betadex, can be used as the pharmaceutically acceptable polymeric substrate. These substrates are able to bind nicotine or a pharmaceutically acceptable nicotine derivative, as well as the pharmaceutically acceptable inorganic cations. In addition, these substrates are well known for use in pharmaceutical products, for oral administration as well as for transdermally administration.

In a preferred embodiment, the nicotine-containing product of the present invention comprises less than 20 wt % of nicotine or the pharmaceutically acceptable nicotine derivative, preferably 8-18 wt %, most preferably 10-15 wt %. Thanks to these relatively low nicotine contents, undesired side effects such as a bitter taste or irritation of the treatment area can be avoided.

Preferably, the nicotine-containing product comprises nicotine itself. The resorption of nicotine in the free base form is more rapid than in the form of a derivative, such as a salt.

In a preferred embodiment, the pharmaceutically acceptable Inorganic cation is selected from the group consisting of $Li^+$, $K^+$, $Na^+$, $Mg^{2+}$, $Ca^{2+}$, $Fe^{2+}$, $Zn^{2+}$, and mixtures thereof. Of theses cations, $Mg^{2+}$, $Ca^{2+}$, $Fe^{2+}$, and/or $Zn^{2+}$ are particularly advantageous. Preferably, the nicotine-containing product comprises 1-10 wt % of the pharmaceutically acceptable inorganic cation. This cation content guarantees that the nicotine content is low enough to avoid adverse side effects but high enough to achieve the desired nicotine release.

In a further aspect, the present invention pertains to a method for producing a nicotine-containing product. The method comprises the steps of
(a) pre-treating the substrate with a pharmaceutically acceptable inorganic or organic salt in the presence of a solvent at a temperature of 10-30° C. for a period of 5-60 minutes;
(b) treating the pretreated substrate of step (a) with nicotine or a pharmaceutically acceptable nicotine derivative at a temperature of 10-30° C. for 5-60 minutes; and
(c) removing the solvent.

Pre-treating the polymeric substrate with a pharmaceutically acceptable inorganic or organic salt in the presence of a solvent leads to incorporation of inorganic cations into the substrate. By the later application of nicotine or a nicotine derivative, the desired nicotine content is reached. The method of the present invention allows for a very easy and straight forward preparation of a nicotine-containing product, which can be used for the production of a pharmaceutical product.

In a preferred embodiment, the pharmaceutically acceptable inorganic or organic salt is selected from the group consisting of $LiOAc$, $Li_3PO_4$, $Li_2HPO_4$, $LiH_2PO_4$, $LiCl$, $LiOH$, $NaCl$, $KOH$, $NaOH$, $Na_3PO_4$, $Na_2HPO_4$, $NaH_2PO_4$, $Mg(OH)_2$, $MgCl_2$, $Mg(OAc)_2$, $Mg(CO_2)_2$, $MgHPO_4$, $MgSO_4$, $Ca(OH)_2$, $CaCl_2$, $Ca(OAc)_2$, $Ca(CO_2)_2$, $CaHPO_4$, $CaSO_4$, $FeCl_2$, $Fe_3(PO_4)_2$, $FeHPO_4$, $Fe(OH)_2$, $FeSO_4$, $Fe(CO_2)_2$, $Fe(OAc)_2$, $Zn(OAc)_2$, $ZnSO_4$, $Zn(OH)_2$, $ZnCl_2$, and mixtures thereof. These salts are all water soluble and are known to be pharmaceutically acceptable. In a particularly preferred embodiment, $Ca(OH)_2$ is used.

In a preferred embodiment, the solvent used for the method for producing the nicotine-containing product is selected from the group consisting of water, ethanol, methanol, 2-propanol, and mixtures thereof; preferably water and/or ethanol. These solvents are known to be pharmaceutically inoffensive and, in addition, have very good solution properties with regard to inorganic salts and to nicotine and nicotine derivatives. On the other hand, the described polymeric substrates are not soluble in these solvents, so that the nicotine-containing product can easily be separated from the solvent, by filtration, for instance.

In a further aspect, the present invention also relates to the use of the nicotine-containing product for the preparation of nicotine-containing pharmaceutical product. Such a nicotine-containing pharmaceutical product is usually obtained by addition of the nicotine-containing product of the present invention to a base material, such as a gum or gel. In addition, additives such as sweeteners, binding agents, separating agents, lubricants, coloring agents, flavor additives, acids, effervescent agents, antioxidants, glidants and/or preservatives may be added. The nicotine-containing product is preferably used for the preparation of a nicotine-containing pharmaceutical product intended for oral or transdermal administration.

EXAMPLES

The following non-limiting examples will illustrate representative embodiments of the invention in detail.

Example 1

Preparation of Nicotine-Polacrilex (10%)-Calcium

In a 2 l roundbottom flask, 100 g Amberlite IRP-64 (Polacrilex) was suspended in 250 g deionized water. The suspension was stirred at 25° C. for 10 min. A suspension of 5.20 g $Ca(OH)_2$ in 50 g deionized water was added. The resulting mixture was stirred for 30 min, during which time the internal temperature was controlled to be at 20-30° C. 11.6 g nicotine puriss. was added and the addition flask was rinsed with 10 g deionized water. The resulting thick suspension was stirred at 25° C. for at least 30 min. The solvent was removed under reduced pressure using a rotary evaporator at 70-80° C. The resulting white powder was dried for 2 hours in vacuo at 70-80° C. to yield 88.0 g of Nicotine-Polacrilex (10%)-Calcium complex.

Example 2

Preparation of Nicotine-Polacrilex (15%)-Calcium

In a 2 l roundbottom flask, 100 g Amberlite IRP-64 (Polacrilex) was suspended in 250 g deionized water. The suspension was stirred at 25° C. for 10 min. A suspension of 5.20 g $Ca(OH)_2$ in 50 g deionized water was added. The resulting mixture was stirred for 30 min, during which time the internal temperature was controlled to be at 20-30° C. 17.4 g nicotine puriss. was added and the addition flask was rinsed with 10 g deionized water. The resulting thick suspension was stirred at 25° C. for at least 30 min. The solvent was removed under reduced pressure using a rotary evaporator at 70-80° C. The resulting white powder was dried for 2 hours in vacuo at 70-80° C. to yield 80.0 g of Nicotine-Polacrilex (15%)-Calcium complex.

Example 3

Preparation of Nicotine-Polacrilex Complexes Comprising Other Inorganic Cations

In analogy to examples 1 and 2, various nicotine-polacrilex complexes with other inorganic cations have been prepared, using NaCl, NaOH, $Na_3PO_4$, KOH, $Mg(OH)_2$, $Ca(OH)_2$, $CaCl_2 \times 2\, H_2O$, $CaSO_4 \times 2\, H_2O$, $Ca(CO_2)_2 \times H_2O$, $Ca(OAc)_2 \times H_2O$, and $CaHPO_4$.

Example 4

Nicotine Release of Nicotine-Polacrilex Complexes

For the determination of the nicotine release rates, the nicotine-polacrilex complexes were suspended in a 1 M aqueous NaCl solution according to Ph. Eur. 5.0 (2005). The suspension was shaken for 10 min at 37° C. and then filtered. The nicotine content of the filtrate was measured and the release rate of nicotine was determined based thereon. The results are shown in table 1.

TABLE 1

| | Nicotine content (wt %) | Salt | Cation content | Nicotine release in 10 min (%) |
|---|---|---|---|---|
| 1[1] | 10.3 | — | — | 65.13 |
| 2[1] | 11.0 | — | — | 62.73 |
| 3[1] | 12.0 | — | — | 62.34 |
| 4[1,2] | 15.5 | — | — | 65.92 |
| 5 | 10.5 | NaCl | 3.3 | 70.80 |
| 6 | 10.5 | NaOH | 3.3 | 71.60 |
| 7 | 10.3 | $Na_3PO_4$ | 3.3 | 68.10 |
| 8 | 10.8 | KOH | 5.5 | 70.10 |
| 9 | 10.9 | $Mg(OH)_2$ | 1.7 | 68.00 |
| 10 | 9.3 | $Ca(OAc)_2$ | 2.8 | 67.00 |
| 11 | 10.2 | $Ca(CO_2)_2$ | 2.8 | 68.88 |
| 12 | 9.4 | $CaHPO_4$ | 2.8 | 69.31 |
| 13 | 9.8 | $CaSO_4$ | 2.8 | 63.19 |
| 14 | 8.7 | $CaCl_2$ | 2.8 | 65.21 |
| 15 | 10.6 | $Ca(OH)_2$ | 2.8 | 71.33 |
| 16 | 10.4 | $Ca(OH)_2$ | 2.8 | 72.72 |
| 17 | 10.6 | $Ca(OH)_2$ | 2.8 | 73.60 |
| 18 | 10.5 | $Ca(OH)_2$ | 2.8 | 79.90 |
| 19 | 10.4 | $Ca(OH)_2$ | 2.8 | 80.80 |
| 20 | 14.7 | $Ca(OH)_2$ | 2.8 | 82.30 |

[1]Comparative examples;
[2]taken from US 2003/0224048

The invention claimed is:

1. A method for producing a nicotine-containing product, comprising steps of:
   (a) pre-treating a pharmaceutically acceptable polymeric substrate with a pharmaceutically acceptable inorganic or organic salt having an inorganic cation in the presence of a solvent at a temperature of 10-30° C. for a period of 5-60 min;
   (b) treating the pre-treated substrate of step (a) with nicotine or a pharmaceutically acceptable nicotine salt at a temperature of 10-30° C. for 5-60 min; and
   (c) removing the solvent,
   wherein:
   the pharmaceutically acceptable polymeric substrate is Amberlite® IRP-64 or betadex; and
   the pharmaceutically acceptable inorganic or organic salt having an inorganic cation is $Ca(OH)_2$.

2. The method for producing a nicotine-containing product according to claim 1, wherein the solvent is selected from the group consisting of water, ethanol, methanol, 2-propanol, and mixtures thereof.

3. The method for producing a nicotine-containing product according to claim 1, wherein the pre-treated substrate of step (a) is treated with nicotine in step (b).

4. A nicotine-containing product obtainable by the method according to claim 1.

5. The nicotine-containing product according to claim 4, comprising less than 20 wt % of nicotine or the pharmaceutically acceptable nicotine salt.

6. The nicotine-containing product according to claim 4, comprising 1-10 wt % of the inorganic cation.

7. A nicotine-containing pharmaceutical product comprising the nicotine-containing product produced according to claim 4.

8. The nicotine-containing pharmaceutical product according to claim 7, wherein the product is suitable for oral administration.

9. The nicotine-containing pharmaceutical product according to claim 7, wherein the product is suitable for trans-dermal administration.

* * * * *